US006895341B2

(12) United States Patent
Barrey et al.

(10) Patent No.: US 6,895,341 B2
(45) Date of Patent: May 17, 2005

(54) METHOD FOR ANALYZING IRREGULARITIES IN HUMAN LOCOMOTION

(75) Inventors: Eric Barrey, Barbizon (FR); Bernard Auvinet, Laval (FR)

(73) Assignee: Institute National de la Recherche Agronomique, Paris (FR)

( * ) Notice: Subject to any disclaimer, the term of this patent is extended or adjusted under 35 U.S.C. 154(b) by 160 days.

(21) Appl. No.: 10/181,952

(22) PCT Filed: Feb. 5, 2001

(86) PCT No.: PCT/FR01/00340

§ 371 (c)(1),
(2), (4) Date: Nov. 8, 2002

(87) PCT Pub. No.: WO01/56470

PCT Pub. Date: Aug. 9, 2001

(65) Prior Publication Data

US 2003/0139692 A1 Jul. 24, 2003

(30) Foreign Application Priority Data

Feb. 4, 2000 (FR) .............................................. 00 01461

(51) Int. Cl.$^7$ ................................................ A61B 5/103

(52) U.S. Cl. ........................................ 702/32; 708/400

(58) Field of Search ........................... 702/32; 623/912; 708/5, 400

(56) References Cited

U.S. PATENT DOCUMENTS 6,707,454 B1 * 3/2004 Barg et al. .................. 345/440
6,747,650 B2 * 6/2004 Turner et al. ............... 345/473

OTHER PUBLICATIONS

Tamura et al., Classification of Acceleration Waveforms During Walking by Wavelet Transform, Methods of Information in Medicine, 1997, Full Text, see all.*
Waarsing et al., Quantifying the Stability of Walking Using Accelerometers, 18th Annual International Conference of the IEEE Engineering in Medicine and Biology Society, 1996, pf 469.*
Veltink et al., Detection of Static and Dynamic Activities Using Uniaxial Accelerometers, IEEE Transactions on Rehabilitation Engineering, Dec. 1996, all.*
Karcnik, Gait Dynamic Stability Assessment in a Sagittal Plane, 18th Annual International Conference of the IEEE Engineering in Medicine and Biology Society, 1996, pf 467.*
Mayagoitia et al., Evaluation of Balance During Activities of Daily Living, Proceedings of the First joint BMES/EMBS Conference Serving Humanity, Advancing Technology, Oct. 13, 1999, p. 520.*
Mayagoitia et al., 18th Annual International Conference of the IEEE Engineering in Medicine and Biology Society, 1996, pf 573.*

(Continued)

Primary Examiner—Patrick Assouad
Assistant Examiner—Craig Steven Miller
(74) Attorney, Agent, or Firm—Jacobson Holman PLLC

(57) ABSTRACT

The invention relates to a method of analysis for human locomotion irregularities. In such method, acceleration measurements obtained during one or more motions controlled at a stabilized gait of a human being are used, through accelerometers measuring on a time base accelerations according to at least one direction, and any locomotion irregularities are analyzed from reference measurements.

Such measured accelerations are submitted to at least one wavelet transformation and the resulting wavelet transform is used to detect and/or analyze the irregularities.

18 Claims, 15 Drawing Sheets

OTHER PUBLICATIONS

Verplaetse, inertial Proprioceptive Devices: Self–motion–sensing Toys and Tools, IBM Systems Journal, 1996, pp. 639–650.*

Larsson, Global Positioning System and Sport–Specific testing, Sports Medicine, 2003, pp. 1–4.*

Sekine M et al: "Classification of acceleration waveform in a continuous walking record" Proceedings of the 20th Annual Int'l. Conference of the IEEE Engineering in Medicine and Biology Society, vol. 20, No. 3, Oct. 29, 1998–Nov. 1, 1998. pp. 1523–1526.

Database Inspec 'Online! Institute of Electrical Engineers, Stevenage, GB; Tamura et al; "Classification of acceleration waveforms during walking by wavelet transform" & Biosignal Interpretation II, Kanagawa, Japan, Setp. 1996, vol. 36, No. 4–5, pp. 356–359, Methods of Information in Medicine, Dec. 1997, F.K. Schattauer Verlagsgesellschaft, Germany.

* cited by examiner

METHOD FOR ANALYZING IRREGULARITIES IN HUMAN LOCOMOTION

This is a nationalization of PCT/FR01/00340 filed Feb. 5, 2001 and published in French.

The present invention relates to a method of analysis for human locomotion irregularities.

The invention concerns indeed the analysis of the human walking in the medical and paramedical practice, more particularly to study walking degradation and perform fall predictions so as to implement prevention measures, for example with elderly persons. The invention is also applied to claudication measurements following traumas or medical or surgical treatments. Another application field is sport walking or running.

Two complementary families of techniques have been developed to study the motions of the human body and the mechanics thereof and have allowed to increase considerably the knowledge on the human locomotion physiology:
  kinematics methods that measure motions of body parts and articular angles with the help of cinema or video images, and
  dynamical methods that measure forces or accelerations acting on body parts.

The kinematics methods are descriptive and bring numerous details on the motions of each body segment, but are difficult to implement. The dynamical methods are more explicative, since they give information on the mechanical actions causing the motion. They give that way more synthetic information which is nevertheless very fine.

Various known measuring devices implemented in the dynamical methods (also called kinetics) are baropedometric soles, force platforms and accelerometers. The baromedometric soles can provide a clinician with useful data, but are not a force-measuring device. The force platforms for their part give reliable and precise information, but the equipment is cumbersome and expensive. Moreover, their sizes only allow for a single bearing, which give truncated information and does not allow for an analysis of the walking variability.

The accelerometers consisting in sensors being sensitive to instantaneous speed variations have not the above-mentioned disadvantages and allow to obtain precise and reliable results. See particularly the article from AUVINET Bernard, CHALEIL Denis and BARREY Eric, "Analyse de la marche humaine dans la pratique hospitalière par une méthode accélérométrique", REV. RHUM. 1999, 66 (7–9), pp. 447–457 (French edition) and pp. 389–397 (English edition).

Measuring accelerations has this advantage to provide sensitive and detailed information on the forces causing motions and can be simple to implement. Moreover, conditioning and treating data are economical with respect to the use of images. Further, acceleration measurements allow to find all the kinetics and kinematics characteristics of a motion.

The treatment of the results obtained to detect and analyze any locomotion irregularities rests generally on Fourier transforms. The above-mentioned article from AUVINET and al. also proposes calculations based on the signal autocorrelation function (study of the symmetry and regularity of the strides) completed by a z Fischer transform to reach Gauss distributions.

A disadvantage of the frequency analyses (as performed by fast Fourier transforms) is that they need a minimum number of points to provide information sufficiently precise in frequency and energy. Moreover, they do not authorise a time location of a particular event causing a quick frequency change of the acceleration signal. Thus, it is not possible to detect a stumble being isolated amongst other regular steps. The frequency analysis is also badly adapted for time irregularities of the locomotive cycle, which are not stationary, but have chaotic properties (being impredictable at short and long term).

As far as the calculation methods based on the autocorrelation functions are concerned, they allow for a very good detection of periodic dynamical asymmetries, but are little successful to detect irregularities that are neither stationary nor periodic. They do not allow either to identify an isolated event as a sport running default or a stumble.

Moreover, several specific techniques have been developed to study complex motions in the equine locomotion also based on acceleration measurements. However, the motions being studied consist in jumps of sport horses or gait transitions of dressage horses (change from trot to gallop and vice versa), hence in transient motions. Such techniques do not apply to stabilised gait motions, such as human walking or running.

The present invention relates to a method of analysis for human locomotion irregularities based on acceleration measurements, which allows to detect locomotive cycles being abnormal and irregular in time.

The method according to the invention does not require a priori mathematical properties of the studied signals, such as those needed for Fourier transforms (stationary state, periodicity).

Moreover, the method according to the invention may allow for a quick and simple analysis for the results obtained.

An object of the invention is also an analysis method being able to give quantitative complementary information on the lack of dynamical regularity in walking or running cycles.

To this end, the invention applies to a method of analysis for human locomotion irregularities, wherein acceleration measurements obtained during at least one motion controlled at a stabilised gait of a human being are used, through at least one accelerometer measuring on a time base at least one acceleration according to at least one direction, by detecting and analysing any locomotion irregularities from reference measurements.

According to the invention, measured accelerations are submitted to at least one wavelet transformation and the resulting wavelet transform is used to detect and/or analyse the irregularities.

By "stabilised gait", it is meant a repetitive approximately periodic motion (such as walking or running) in contrast with a transient motion.

Surprisingly, the wavelet transformation allows to locate abnormalities with the passing time for such a stabilised gait. Even an isolated stumble may be detected amongst regular steps. Such a method is thus able to detect very short irregularities in contrast with the known methods based on Fourier transforms.

Preferentially, a spectrum of the wavelet transform is visualised in three dimensions, respectively, of time, frequency and spectral energy module of the wavelet transform to detect and analyse the irregularities.

The spectral energy module of the wavelet transform is then advantageously represented by coloured contours or a colour gradient. Further, a linear scale for time and a logarithmic scale for frequency are advantageously used.

The direct visualisation of the wavelet offers a great reading simplicity and allows to identify directly irregularities upon a graphic reading.

Preferentially, the wavelet transform is continuous, such a transform being advantageously a Morlet wavelet transform. Such symmetrical wavelets are well adapted for low frequency analyses, such as body accelerations near the centre of gravity. They are given by the following mathematical formula (function $\Psi$ of variable x):

$$\Psi(x) = k.\exp(-x^2/2).\cos(\omega_0 x)$$

wherein k is a normalisation constant and $\omega_0$ is the pulse of the wavelet being considered, preferentially comprised between 5 and 6 included. An acceleration function Acc being dependant on time t is decomposed over a family of wavelets of such a type by the formula:

$$C(a, b) = \sum_{-\infty}^{+\infty} Acc(t).\Psi(at + b)dt$$

wherein:
the coefficients C give mappings of the function Acc onto the wavelets,
the parameter a is scale parameter (modification of the wavelet stretching), and
the parameter b is a translation parameter (time translation of the wavelets).

In a alternative embodiment, the transform being used is a discrete wavelet transform, such as a Daubechie wavelet transform, preferably of order 5. Such last wavelets have this property to be asymmetrical and to have a zero order moment.

In a preferred embodiment, i.e. the wavelet transform having a time-dependant spectral energy, a low frequency band is defined in which the spectral energy for a regular locomotion is mainly concentrated and said irregularities are detected and/or analysed by using the spectral energy outside such band. The frequency band is preferably comprised between 1 Hz and 4 Hz.

The use of such a band makes for example possible two types of analysis that can be complementary:
identification of zones of spectral energy concentrations outside the band, and
spectral energy quantification out of such band.

Thus, advantageously, irregularities are identified and/or analysed by locating and/or studying the spectral energy peaks outside the band.

Thus, for a pathological walking, high frequency peaks with a significant energetic density exceeding the upper limit of the frequency band (for example 4 Hz) may be observed, such peaks being more or less periodical and regular in time and frequency. Graphic irregularities in the shape of such peaks are indicative of alterations in walking dynamics and regularity.

Moreover, a locomotion irregularity degree is advantageously calculated by reporting the margin spectral energy outside the band to the total spectral energy.

Consequently, for a pathological walking, it can be considered that the margin energy above 4 Hz is higher than 6%.

In another advantageous analysis type based on the low frequency band, the located spectral energy values exceeding the band are measured, for example in the case of very altered walking with high frequency patterns and quite various shape and energy.

The analyses with a wavelet transform are advantageously associated with other methods giving complementary information in the method of analysis for human locomotion irregularities. Such information is combined with the results obtained through wavelet transforms so as to specify the use mode for wavelets, interpret the results obtained by such wavelets and/or complete the results extracted from the analyses with wavelets.

Thus, in an advantageous embodiment, the analysis methods according to any one of the accelerations are at least in a number of two and to detect and/or analyse the irregularities, at least one vectgram (called "front butterfly") is also used representing the intensity of one of the measured accelerations depending on the intensity of another of the measured accelerations. Chaotic drifts may be thus identified visually with respect to a stationary and periodic rate.

The accelerations used are preferentially a vertical acceleration and a lateral acceleration of the subject.

In a preferred implementation, to detect and/or analyse the irregularities, at least one representation in a phase space is also used, giving the intensity of at least one of the accelerations depending on the intensity of the time derivative of such acceleration or depending on such acceleration time shifted with a predetermined time.

The movement of a stationary and periodic rate towards a chaotic rate can be also identified visually. Advantageously, the acceleration being studied is a vertical acceleration.

In such preferred embodiment, at least one Lyapunov coefficient of the representation in the phase space, preferably the maximum Lyapunov coefficient, is calculated advantageously. Thus, dynamical locomotion irregularities can be quantified, such a coefficient measuring the deviating speed of the acceleration signal orbits within the phase space.

Thus, the maximum Lyapunov coefficient, being calculated on a cranio-caudal accelerometric signal measured at the level of the centre of gravity of a subject, quantifies globally a lack of dynamical regularity in the walking cycles. It allows to detect temporal and dynamical fluctuations of co-ordination with respect to a risk of fall. Such global measurement of walking regularity has a clinical interest for a prediction of the risk of fall with an elderly subject. Walking can be thus considered as pathological when the Lyapunov coefficient being used is higher than a critical value.

Thus, advantageously, it is considered that a co-ordination disorder occurs if the maximum Lyapunov coefficient is higher than 0.4.

The device used for the accelerometers and the acceleration measurements is preferentially conform to what is mentioned in the article from AUVINET et al. supra. In particular, the analysis method admits advantageously the following characteristics, considered separately or according to all their technically possible combinations:
the accelerations are measured with the help of an accelerometric sensor comprising two accelerometers arranged according to perpendicular axes;
the accelerometers are incorporated into a semi-elastic waistband secured to the waist of the subject so that they are applied in the median lumbar region opposite the intervertebral space L3–L4;
the accelerometers are arranged near the centre of gravity of the subject (this latter being located when the person is standing at rest before the second sacral vertebra);
the accelerations are measured according to cranio-caudal and lateral axes of the subject called hereunder, respectively, vertical and lateral axes;
the acceleration measurements are recorded with a portable recorder;

the results obtained with the wavelet transform are completed by obtaining the stride frequency, the step symmetry and regularity, the symmetry and regularity variables being advantageously submitted to a z Fischer transform;

the motions controlled at a stabilised gait consist in a free walking at a comfort speed for the subject over a distance comprised between 25 and 50 m, preferably equal to 40 m, advantageously go and back.

Moreover, the following characteristics are advantageously implemented separately or in combination:

the accelerations are thus measured according to a third accelerometer, the three accelerometers being arranged according to perpendicular axes corresponding respectively to the cranio-caudal, lateral and longitudinal (antéro-posterior) axes of the subject;

for the analysis of sport motions, the accelerations measured are cranio-caudal and longitudinal (sagittal plane of the subject) accelerations;

for the analysis of sport motions, measurements are performed during effort tests on track or on conveyor belt;

a complementary Fourier frequency analysis is also implemented in the analysis method by calculating:

the total spectral energy (it decreases for a pathological walking), the relative energy of the fundamental frequency which corresponds to the step frequency (it decreases and is distributed towards higher frequency harmonics for a pathological walking) and/or the spectrum slope calculated by a linear regression equation on a semi-logarithmic representation of the squared spectral energy depending on the frequency (such slope is all the more negative since walking is altered in its temporal and dynamical regularity).

Moreover, a sensor comprising the accelerometers, a recorder and an event-marking device provided to mark events on the recorded acceleration signals and/or synchronize the acceleration recordings with other measuring devices (video or cinema camera, force platform, timing cell, EMG device, etc.) are advantageously used. Such device is advantageously arranged between the sensor and the recorder and advantageously integrated into a recording housing of the recorder.

The event-marking device has preferably activation inputs consisting in manual electrical, optoelectronic (cell sensitive to a light flash) and/or electronic contacts.

It has preferably outputs consisting in:

a square wave emitter having advantageously a maximum value (saturation) of a period comprised between 10 and 50 msec and preferably 10 msec for a signal acquisition frequency at 100 Hz advantageously emitted on the acceleration signal tracks so as to mark such signal on a measuring point;

a plurality of red luminescent diodes (LED) being lightened to provide a light signal visible on a single image with a video camera, advantageously during a period comprised between 10 and 50 msec, preferably equal to 10 msec; and/or a TTL output providing advantageously a squared signal of 5V during a period comprised between 10 and 50 msec, preferably equal to 10 msec.

The use of such an event-marking device is of a particular interest to mark change times (start and arrival in a walking or running test) on acceleration recordings. Thus, a spatial or cinematic marking (synchronized video film) of the recorded motion can be obtained so as to calculate the representative distances for a sport motion.

The invention also relates to the applications of the method:

in the medical field, in particular for the early detection of neuromotor disorders of elderly subjects (it is then particularly interesting to use the maximum Lyaponov coefficient), and in the sport field, in particular for detecting technical defects for sport walkers or runners.

Thus, the method of the invention can be advantageously applied to the detection of particularities of the athlete's stride during a race period, such as the flight time, the bearing time, the symmetry of right and left half-strides, the right and left propulsion and braking forces and the race fluidity index.

The method according to the invention can also be applied to measure and quantify the biomechanical constraints due to a disease of the locomotive apparatus, including as a function of the race speed.

The characteristic of the particularities of the athlete's stride during the race according to the method of the invention is useful particularly to improve the efficiency and performance of the sportsman.

The characterization of the acceleration parameters according to the method of the invention is useful particularly to assess the tolerance for a disease in the locomotive apparatus as a function of the working loads.

The present invention will be illustrated and better understood with particular embodiments, with no limitation, referring to the accompanying drawings, wherein.

Figure 16:
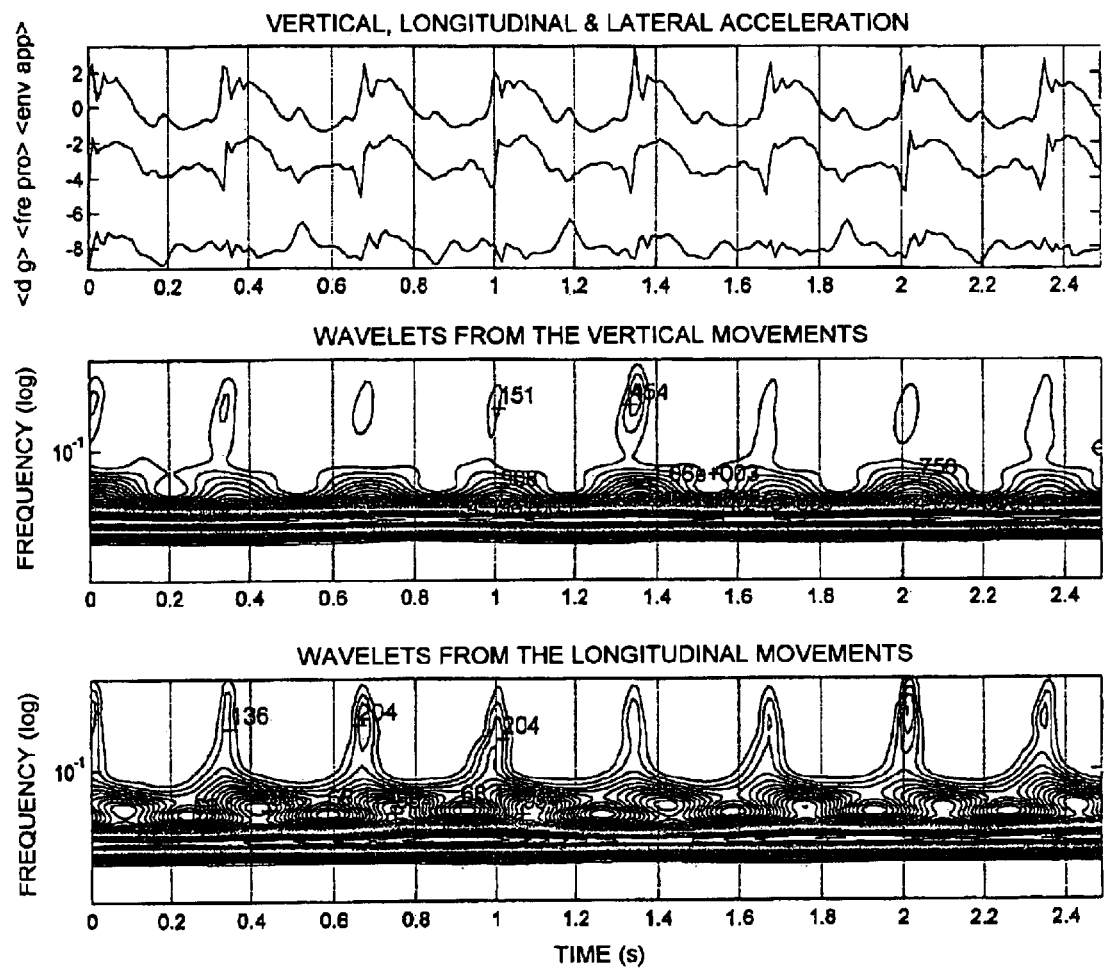
FIG. 16 shows a three dimension spectral image of a Morlet wavelet transform obtained according to the method of the invention in a running period for a sportsman the stride of whom is very fluidic.
Figure 17:
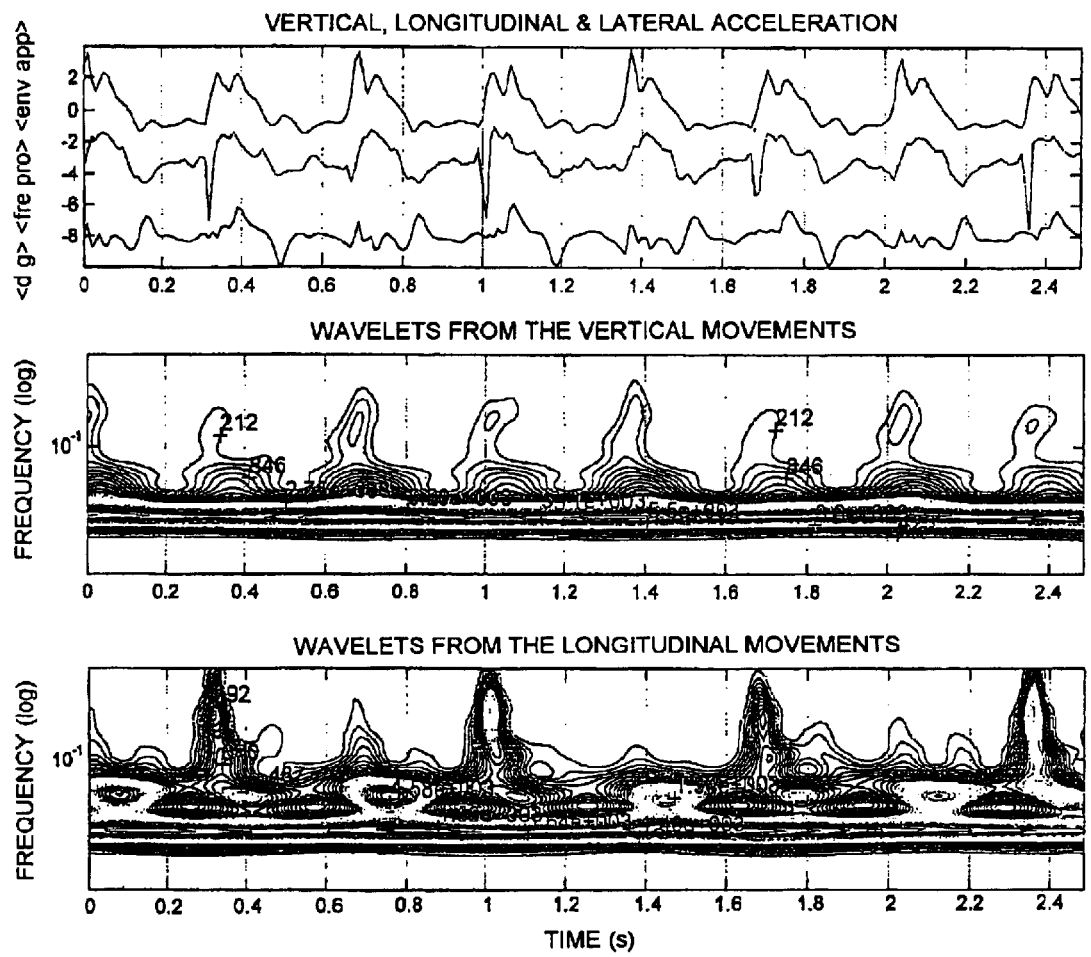
FIG. 17 shows a three dimension spectral image of a Morlet wavelet transform obtained according to the method of the invention in a running period for a sportsman having a strong propulsion and braking asymmetry.

On FIGS. 16 and 17, the upper graph shows the vertical, longitudinal and lateral acceleration curves in the time expressed in seconds; the median graph shows the spectral image of the wavelet transform of the vertical motions in the time; the lower graph illustrates the spectral image of the wavelet transform of the longitudinal motions in the time expressed in seconds.

Figure 18:
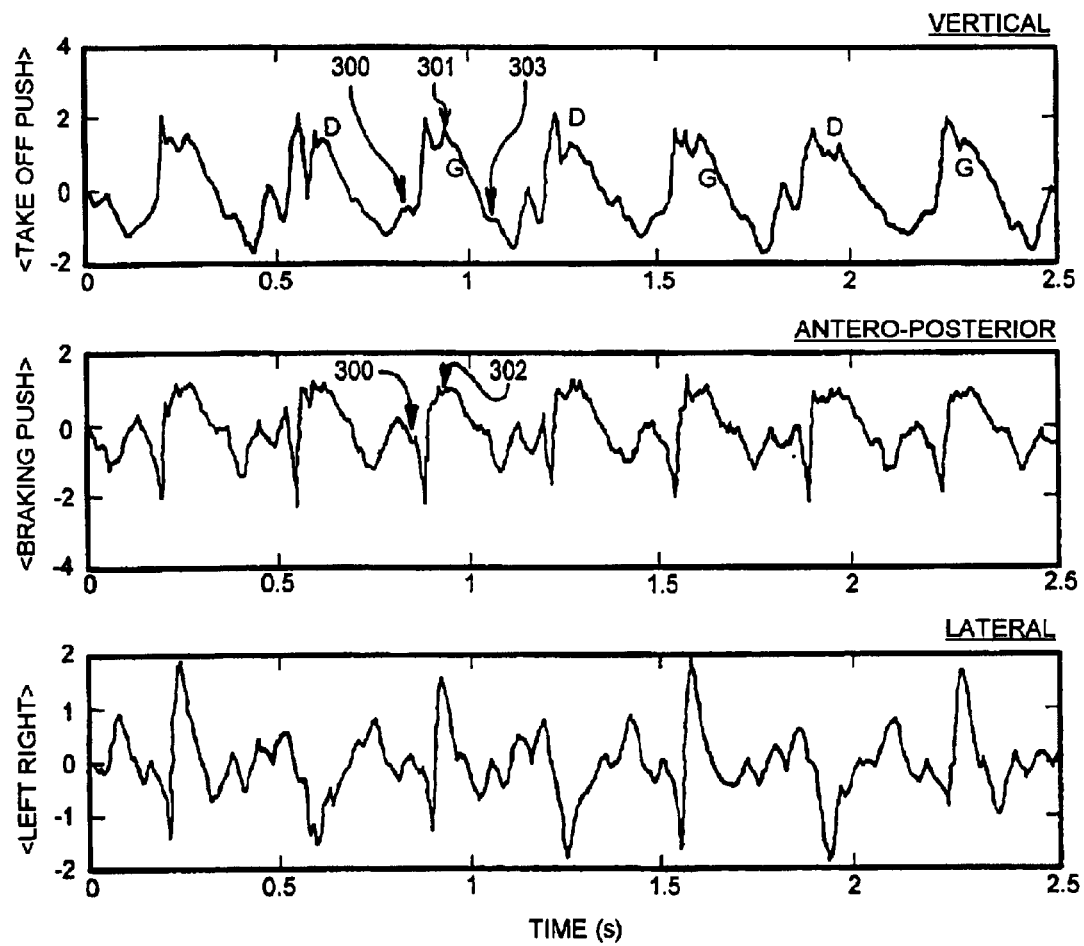

FIG. 18 shows vertical, antero-posterior and lateral acceleration curves in the time synchronized with images of a subject for a regular running stride.

Figure 1:
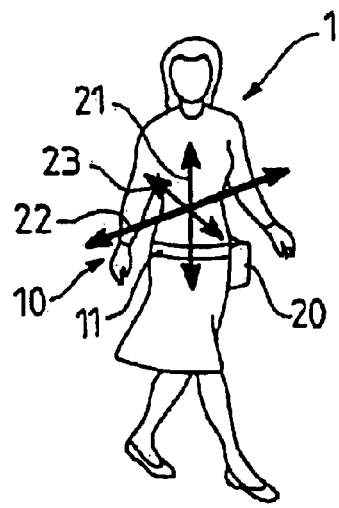
FIG. 1 represents a subject provided with an acceleration sensor for implementing the analysis method according to the invention.

A measuring device 10 (FIGS. 1 and 2) comprises a motion-sensitive sensor 16 connected with an ambulatory recorder 20 formed as a housing.

Figure 4:
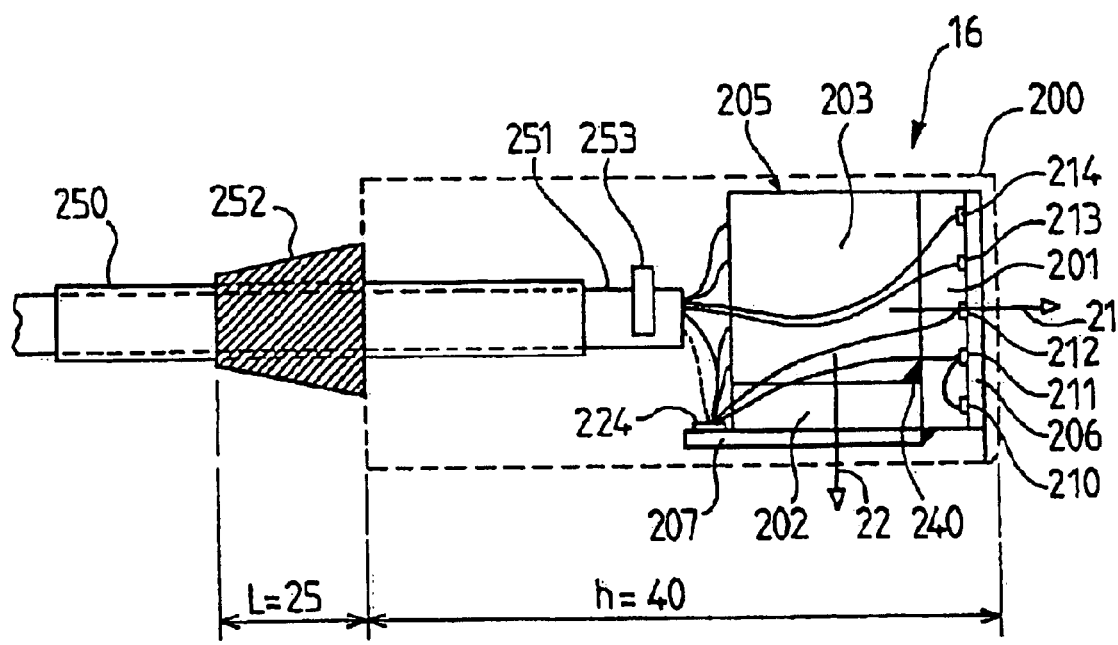
FIG. 4 represents a front sectional view of the sensor of the measuring device of FIG. 2.
Figure 5:
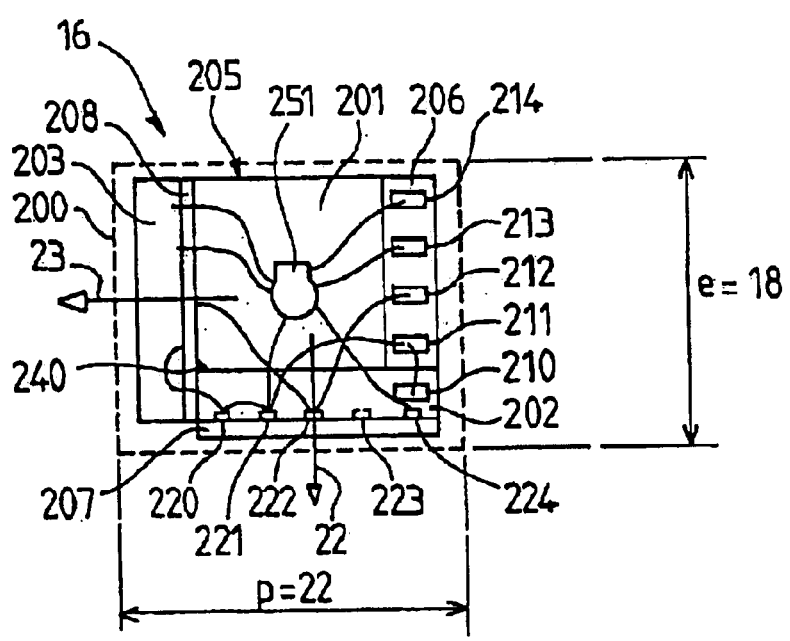
FIG. 5 represents a top sectional view of the sensor of the measuring device of FIGS. 2 and 4.

The sensor 16 is an accelerometric sensor comprising (FIGS. 4 and 5) accelerometers 201, 202 and 203 arranged perpendicularly so as to detect accelerations respectively in the perpendicular directions 21, 22 and 23. As an illustration, the three accelerometers 201, 202 and 203 are oriented respectively according a first cranio-caudal direction 21 (hereafter vertical), according to a second latero-lateral direction 22 and according to a third antero-posterior direction 23 (hereafter longitudinal) of a subject 1. Such accelerometers 210–203 are sensitive to continuous and dynamical components and are adapted for measuring low frequency motions. Their own frequency is for example 1200 Hz, the measuring range being between ±10 g and the sensitivity being 5 mV/g at 100 Hz. They form a cubic assembly 205 in which their orthogonality is provided through squares 240. Such assembly 205 is moulded in a small-size parallelepiped polymer coating 200. The coating 200 is insulating, stiff, protective and waterproof. It has for example a height h (direction 21), a width 1 (direction 22) and a depth p (direction 23) respectively of 40, 18 and 22 mm.

Each of the accelerometers 201, 202 and 203 is provided with five connecting terminals comprising:
 a mass terminal (terminals 210 and 220 respectively of the accelerometers 201 and 202),
 a negative power supply terminal connected with the mass terminal (terminals 211 and 221 respectively of the accelerometers 201 and 202),
 a positive power supply terminal (terminals 212 and 222 respectively of the accelerometers 201 and 202),
 a negative signal terminal (terminals 213 and 223 respectively of the accelerometers 201 and 202), and
 a positive signal terminal (terminals 214 and 224 respectively of the accelerometers 201 and 202).

The terminals and the accelerometers 201 to 203 are supported respectively on ceramic bases 206 to 208.

The mass terminals and the negative power supply terminals of the three accelerometers 201 to 203 are interconnected.

The sensor 16 also comprises a wire 251 with twelve mass braided conductors (metal braid avoiding interference) containing wires originating from the power supply and signal terminals of the three accelerometers 201 to 203. Such wire 251, leading to the recorder 20, is partly surrounded by a semi-rigid thermoretractable sheath 250 entering the coating 200. Such sheath 250 allows to avoid any breaking of the wire. It is moreover bounded outside the coating 200 by a frusto-conical part 252 integral with the coating 200 so as to avoid wire breaking risks. The frusto-conical part 252 has a length L for example equal to 25 mm.

Moreover, the wire 251 is provided with a clip 253 adapted to come in abutting relationship with the sheath 250 in case of the wire 251 sliding in the sheath 250 so as to avoid to tear off the welds.

The sensor 16 is incorporated into a semi-elastic waistband 11 secured to the waist of the subject 1 so that this sensor 16 applies in the median lumbar region opposite the intervertebral space L3–L4. Such positioning of the sensor 16 allows for a good stability of the accelerometers near the centre of gravity of the subject 1, such centre of gravity being located before the second sacral vertebra for a human being standing at rest.

Figure 2:
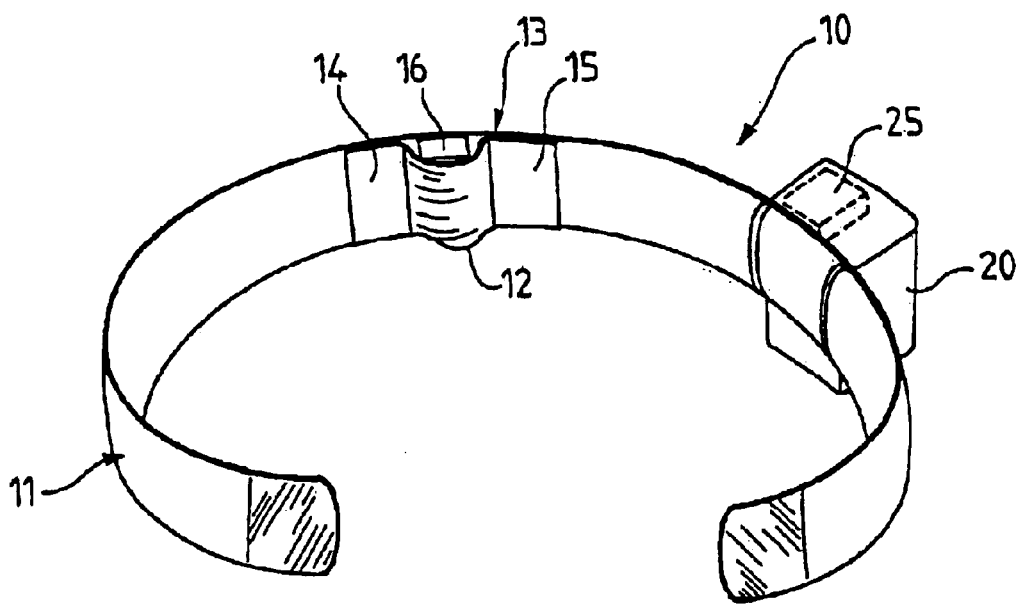
FIG. 2 shows a measuring device useful to implement the analysis method of the invention and corresponding to FIG. 1.
Figure 3:
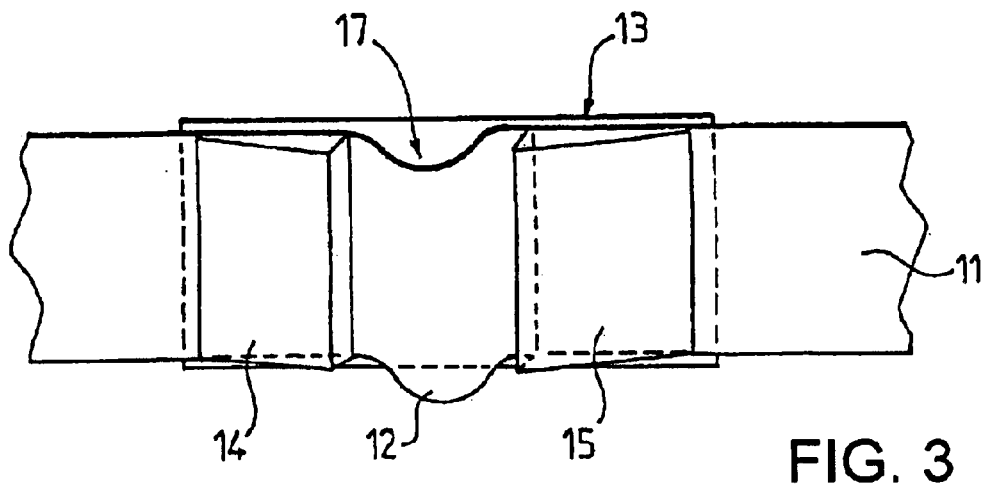
FIG. 3 shows an enlarged part of the measuring device of FIG. 2, with no sensor.

The sensor 16 is arranged within a space 17 formed by a slack part 12 of the waistband 11 and by a leather reinforcement 13 applied against the waistband 11 through wedges 14 and 15 made in a high density foamed fabric arranged on either side of the part 12 (FIGS. 2 and 3). The wedges 14 and 15 allow to position the coating 200 of the sensor 16 precisely within the vertebral groove of the subject 1.

The recorder 20 has for example an acquisition frequency of 100 Hz and an autonomy allowing for a continuous recording during 30 minutes. It is provided with a low-pass filter with a cutout frequency of 50 Hz to avoid any folding phenomena. It receives three perpendicular synchronized tracks. The acceleration measurements are digitized and coded for example on 12 bits.

The recorder 20 comprises connection means with a treatment unit, for example a PC type computer through a serial communication port with the help of a transfer software.

The measuring device 10 also comprises an event-marking device 25 electrically arranged between the sensor 16 and the recorder 20 and integrated into the housing of the recorder 20 (FIG. 2). Such device 25 is adapted for marking events on recorded signals and/or synchronize acceleration recordings with other measuring devices. It is provided with a cell sensitive to a light flash and is adapted for saturating the accelerometric signal for example during 0.01 second for an acquisition at 100 Hz at the time where a flash is triggered.

In operation, the subject 1 is asked to walk on a straight line for example over a distance of 30 m motion and 30 m back. Timing cells are advantageously used, distant by 30 m from the ends of the path followed by the subject so as to be able to measure speeds and synchronize measurements. Such timing cells form each an infrared barrier comprising and emitter and a receiver. They are respectively connected with flashes that are triggered when the infrared barrier is crossed by the subject 1 and are detected by the event-marking device 25.

Figure 6:
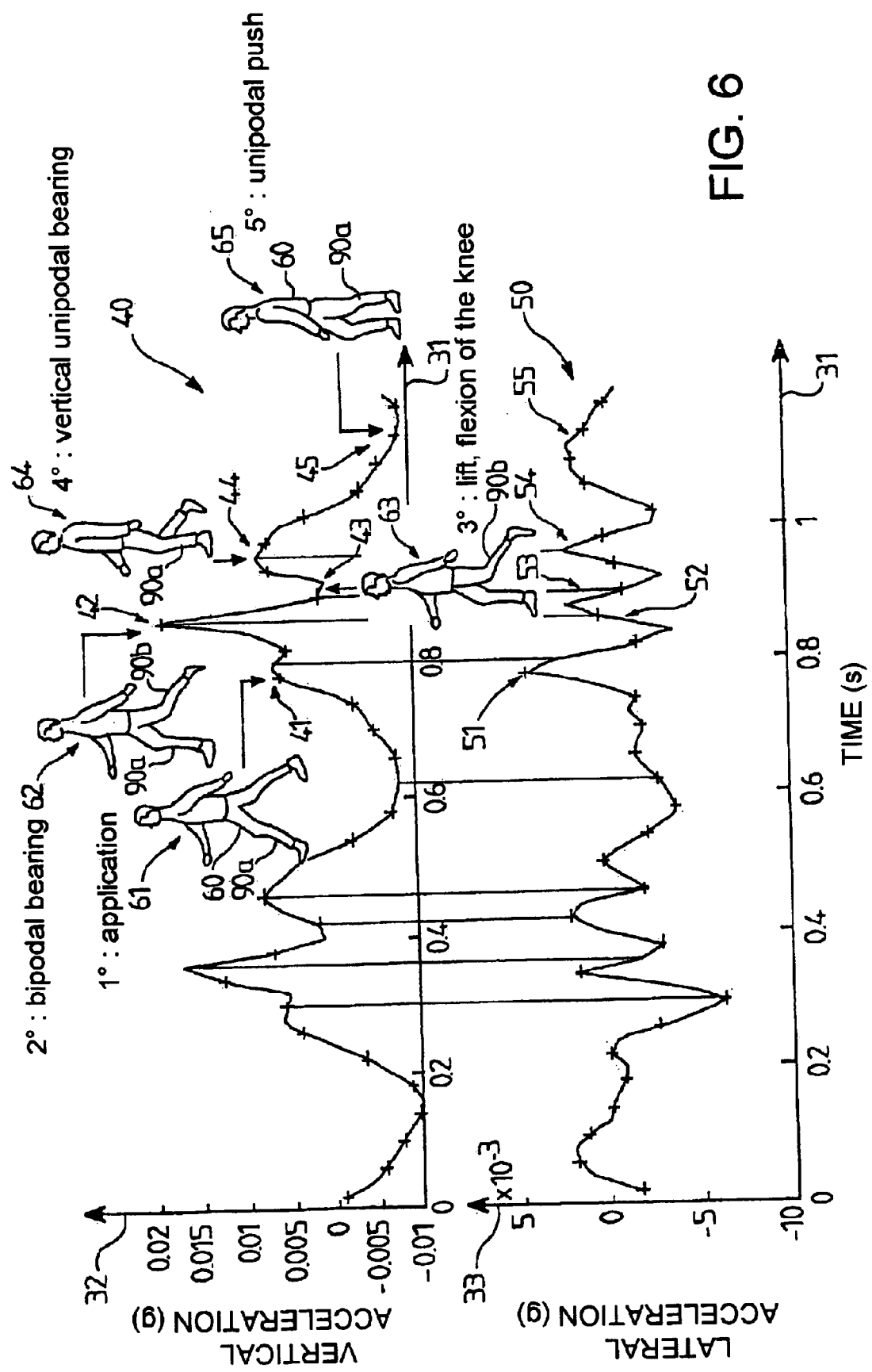
FIG. 6 shows vertical and lateral acceleration curves in the time synchronized with images of a subject for a regular walking stride.
Figure 7:
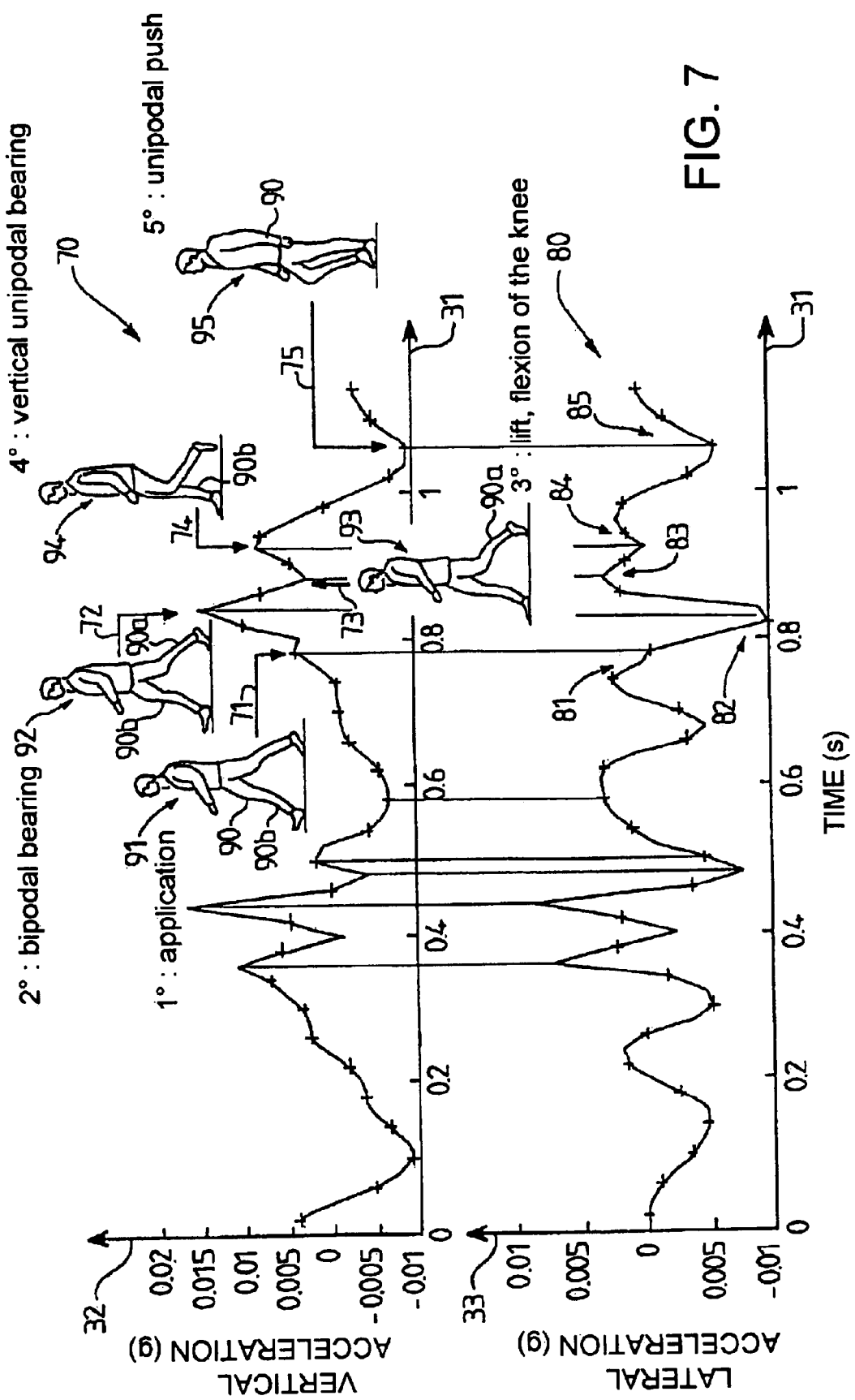
FIG. 7 shows vertical and lateral acceleration curves in the time synchronized with images of a subject for a pathologic walking stride.

Thus, the vertical and lateral accelerations are obtained in the time for a subject 60 having a regular walking stride (FIG. 6) and a subject 90 having a pathological walking stride (FIG. 7)

Thus, for regular walking, a curve 40 is represented giving the vertical acceleration (axis 32, g) and a curve 50 giving the lateral acceleration (axis 33, g) in the time (axis 32, sec). On these curves 40 and 50 different walking steps are identified and they can be put in relation with synchronized images (taken by a video camera) of the walking subject 60. Thus, on the curves 40 and 50:

zones 41 and 51 corresponding to an application of the left leg 90a (image 61), zones 42 and 52 corresponding to a bipodal bearing (image 62), zones 43 and 53 corresponding to a lift of the right leg 90b and a flexion of the right knee (image 63), zones 44 and 54 corresponding to a vertical unipodal bearing of the left leg 90a (image 64), and zones 45 and 55 corresponding to a unipodal push of the left leg 90a (image 65), are marked respectively.

Similarly, the curves 70 and 80 (FIG. 7) representing respectively the vertical and lateral accelerations in the time, on the curves 70 and 80:

zones 71 and 81 corresponding to an application of the right leg 90b (image 91), zones 72 and 82 corresponding to a bipodal bearing (image 92), zones 73 and 83 corresponding to a lift of the left leg 90a and a flexion of the left knee (image 93), zones 74 and 84 corresponding to a vertical unipodal bearing of the right leg 90b (image 94), and zones 75 and 85 corresponding to a unipodal push of the right leg 90b (image 95), are identified respectively.

The method of analysis for human locomotion irregularities based on such results will be described now more in detail. Thus, the attention is drawn onto the curves 100 and 110 (FIG. 6) giving respectively the vertical and lateral accelerations (g, single axis 34 with a translation of −1 g for lateral acceleration) in the time (sec, axes 31 and 35 respectively for vertical and lateral accelerations and reference axis 36). Thus, cycles 101–105 are identified on the vertical acceleration curve 100 and cycles 111–115 on the lateral acceleration curve (FIG. 6) being synchronized and corresponding respectively to motions of the left and right steps.

Similarly, a curve 140 (FIG. 9) is obtained for example, giving the vertical acceleration (axis 32) in the time (axis 31) for a pathological walking, such curve 140 admitting also cycles 141–145.

The vertical acceleration for regular walking and for pathological walking is submitted to a continuous wavelet transform, for example of Morlet type. Such transform is generally expressed by:

$$C(a, b) = \sum_{-\infty}^{+\infty} Acc(t).\Psi(at + b)dt$$

wherein:
the variable t is time,
Acc(t) is the vertical acceleration signal,
the function ψ(at+b) is the wavelet function used for example of Morlet,
the parameters a and b of the wavelet function are respectively the stretching (or scaling) parameter and the wavelet translation parameter, and
the coefficients C(a, b) are the coefficients for the continuous wavelet transform.

Figure 8:
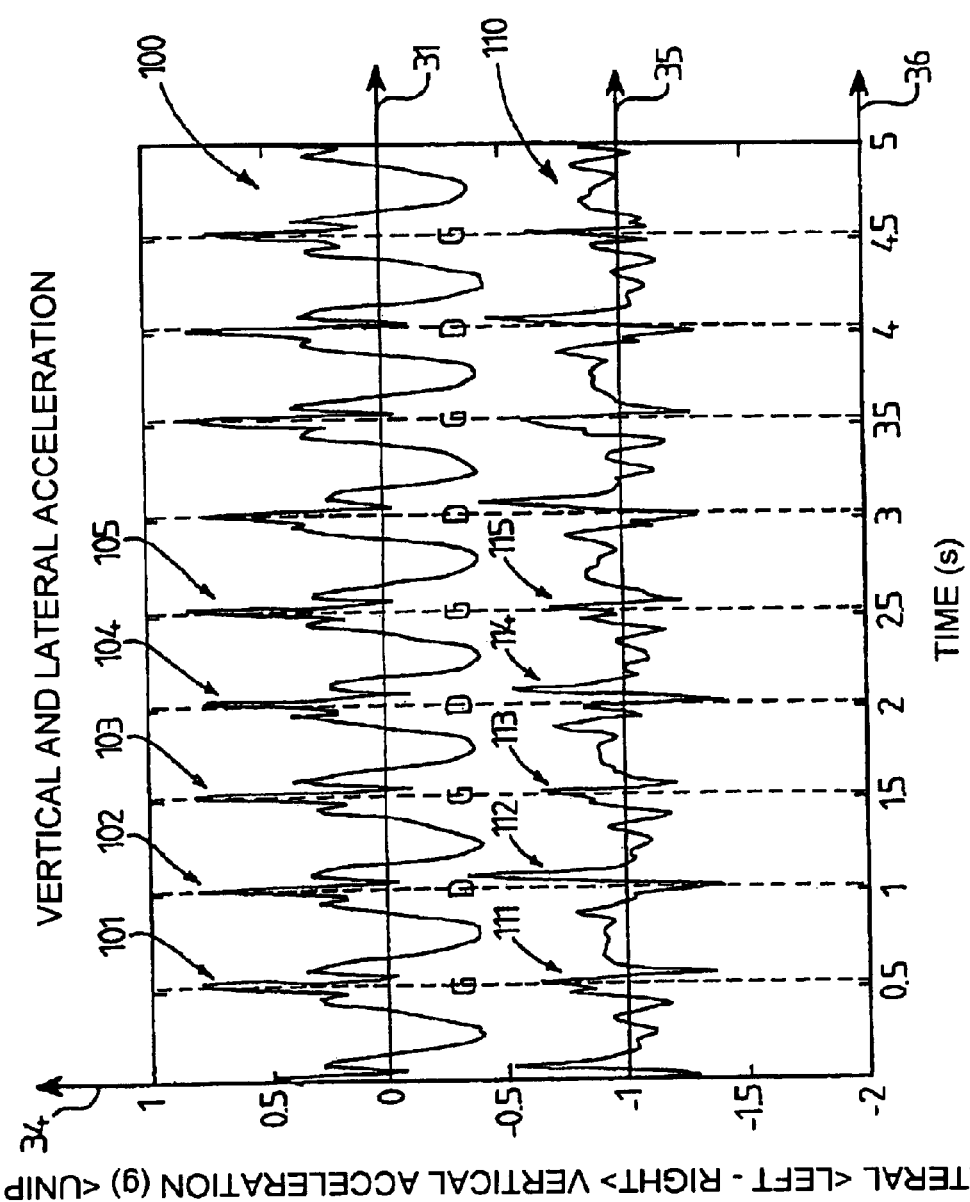
FIG. 8 represents evolution curves in the time for vertical and lateral accelerations for a regular walking of a subject.

From the coefficients C (a, b), for a regular walking, a three dimension spectral image 120 (FIGS. 7 and 8) is built up, corresponding respectively to time, frequency and spectral energy. Such image 120 is represented in a plane time-frequency (or time-scale) with a linear scale for time (axis 3, sec) and a semi-logarithmic scale for frequency (axis 37, Hz). The wavelet energy module ($g^2$) is represented by coloured contours.

Figure 9:
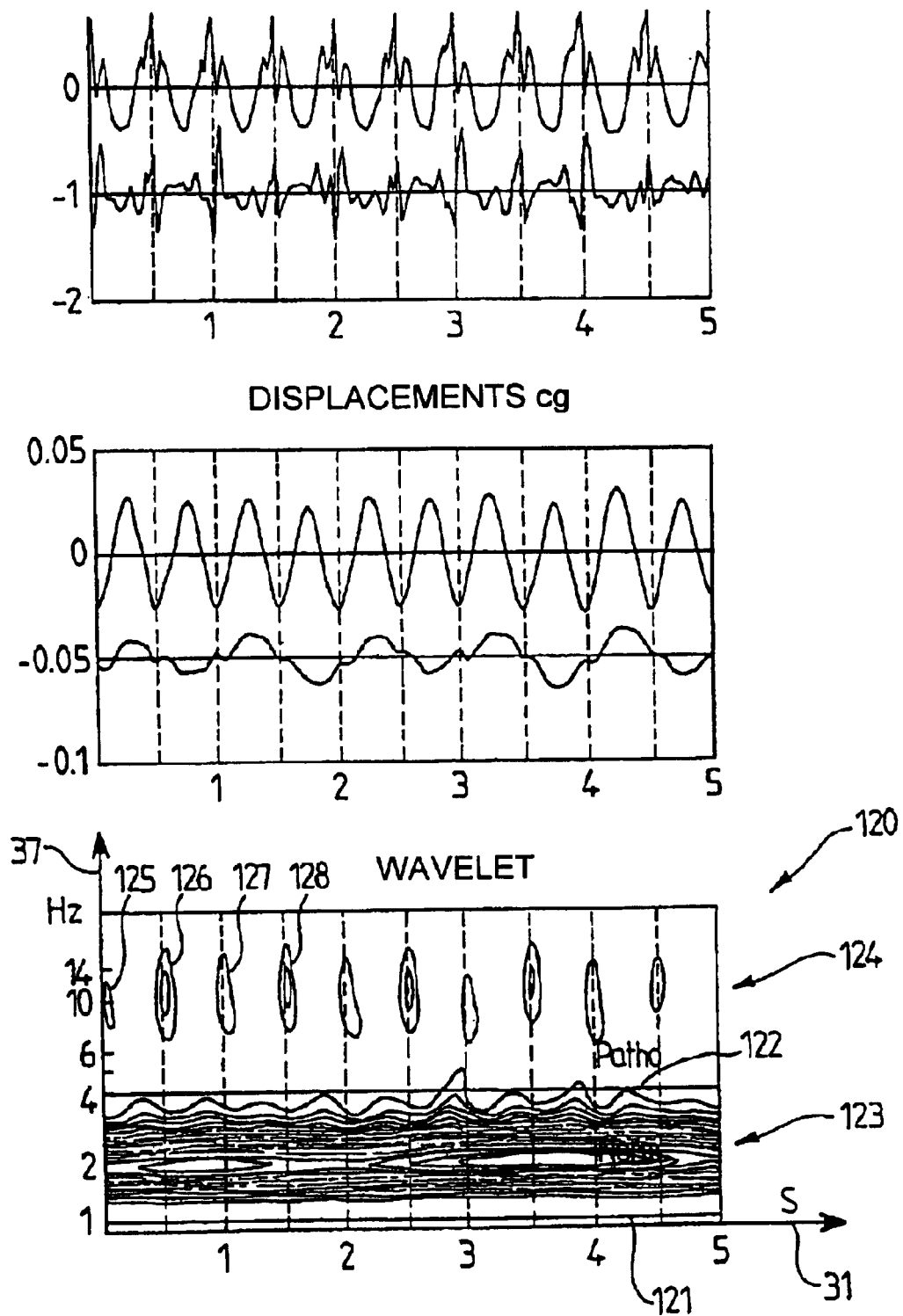
FIG. 9 shows a three dimension spectral image of a Morlet wavelet transform obtained from the vertical acceleration of FIG. 8 according to the analysis method of the invention.

Similarly, a spectral image 150 of the Morlet wavelet transform of the vertical acceleration (FIG. 10) is obtained for pathological walking corresponding to FIG. 9.

The energy density on the enlargement 130 and the spectral image 150 is expressed in acceleration ($g^2$).

On the spectral images 120 and 150 is defined a low frequency band having lower 121 and higher 122 limits associated with values of 1 Hz and 4 Hz. In the case of a regular walking, the spectrum energy density is mainly concentrated within such band. A regular zone 123 comprised within the frequency band and a pathological zone 124 located above this band are more precisely defined.

It is observed in fact that, for a regular walking of the subject (FIG. 7 and enlargement 130 of FIG. 8), the spectral energy is essentially concentrated in the zone 123, periodical low peaks 125–128 appearing in the pathological zone 124 and corresponding to walking cycles of the subject 60.

In contrast, on the spectral image 150 associated with the pathological walking of the subject 90, a fall of the total spectral energy, high frequency peaks 155–158 having a significant energy density exceeding the limit 122 of 4 Hz, and such peaks 155–158 having periodicity and regularity alterations in time and frequency, are observed.

The peaks 155–158 can be interpreted by stating that the more graphically irregular their shape, the more altered are the walking dynamics and regularity.

Besides this graphic information, quantitative information is calculated as explained hereafter. In particular, on the spectral images 120 and 150, the total quantity of spectral energy as well as the margin spectral energy on the frequency axis 37 corresponding to an energy higher than the limit 122 of 4 Hz are determined. The data being accumulated on reference cases show that this margin energy is higher than 6% for a pathological walking.

Thus, for the regular walking of example (FIGS. 7 and 8) a total energy of 22.97 $g^2$ and a margin energy representing 5.3% are obtained and, for the pathological walking (FIG. 10) a total energy of 2.50 $g^2$ and a margin energy representing 15.4%.

In the case of a quite altered walking with high frequency patterns of very different form and energy, the punctual value of the energy module is measured on the spectral image.

Other analysis techniques complete preferably the so-obtained information. In particular, it is interesting to go deeper into the information obtained by a frequency analysis and a calculation of the symmetry and regularity through the autocorrelation function as indicated in the article from AUVINET et al. supra. That way:

a stride frequency of 1.00 stride per second, a stride symmetry of 95.01% with a z Fischer transform of 183.25, and a stride regularity of 186.27 (on 200) with a z Fischer transform of 337.56 are obtained for the regular walking supra.

Figure 10:
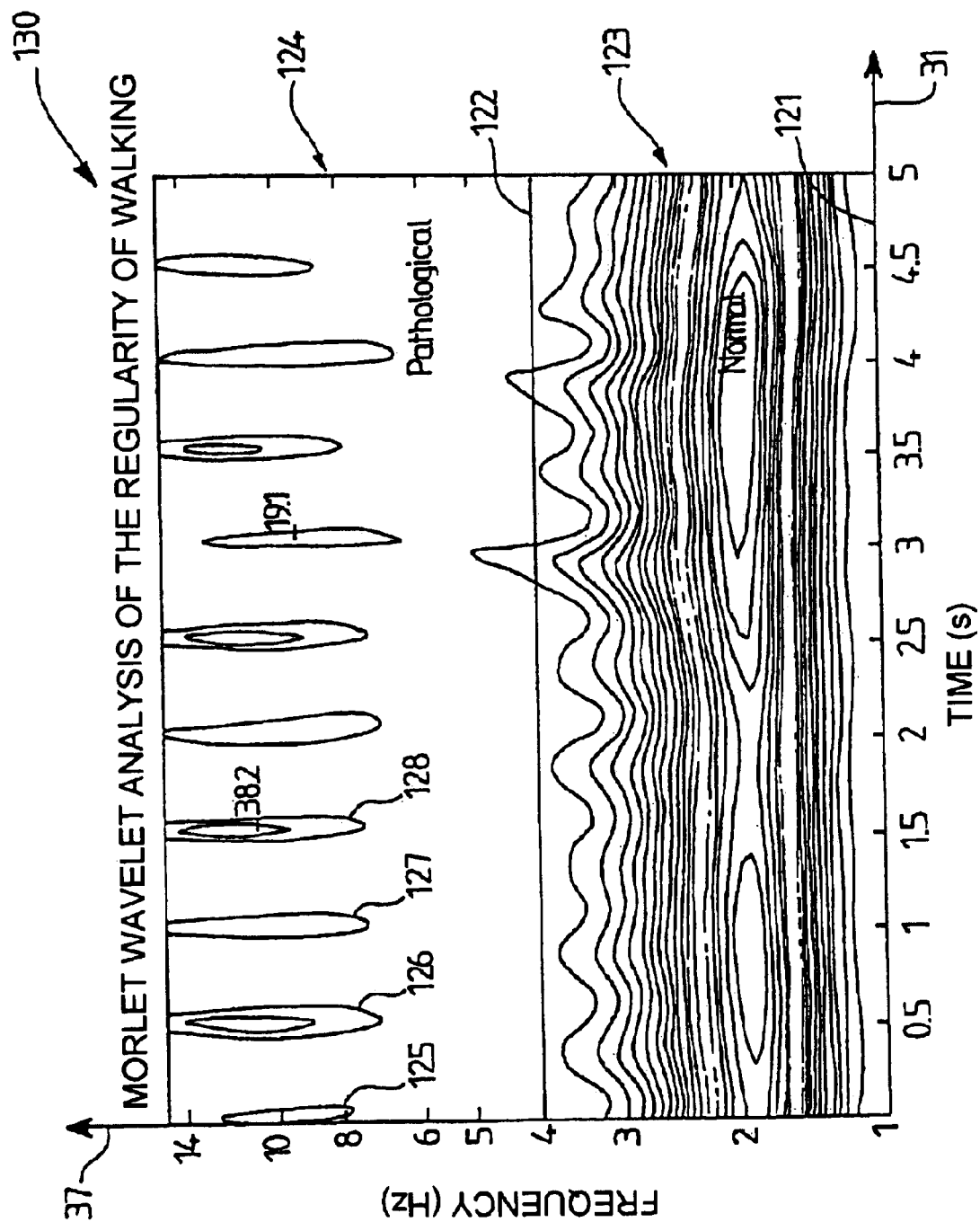
FIG. 10 shows an enlarged spectral image of FIG. 9.

A stride frequency of 0.88 stride per second (too a slow frequency), a stride symmetry of 95.57% with a z Fischer transform of 189.35, and a stride regularity of 160.93 (on 200) with a z Fischer transform of 222.41 (abnormal regularity) are obtained for the pathological walking of the example (FIGS. 9 and 10).

Such results are coupled with those obtained with the wavelet transforms. In particular, the peaks 125–128 or 155–158 are put in relationship with the stride frequency, their right/left alternation with symmetry and their similarity with the stride regularity.

Figure 11:
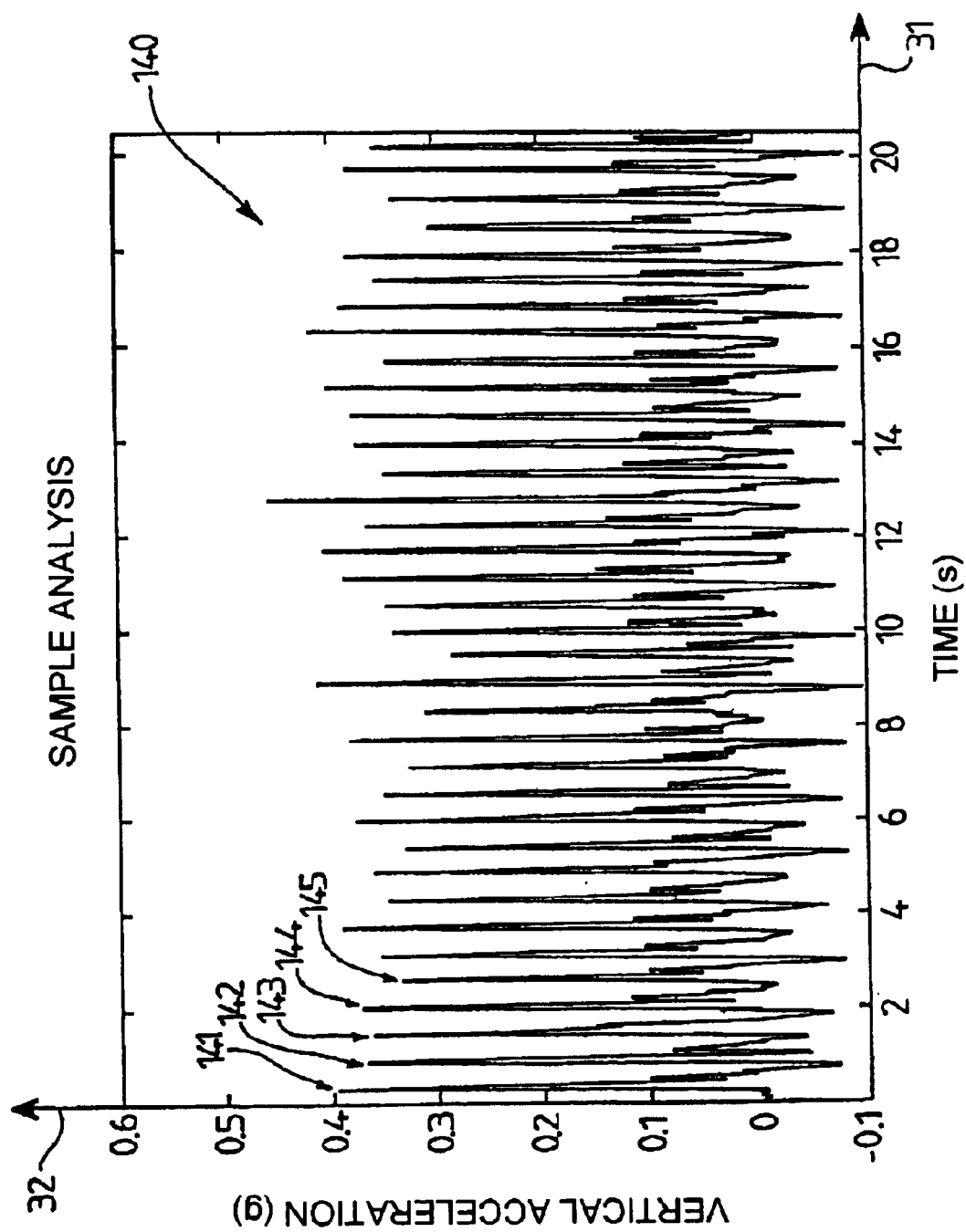
FIG. 11 represents a curve giving the evolution as a function of time of the vertical acceleration for a pathological walking of a falling elderly subject.

Advantageously, such results obtained with wavelet transforms are also completed through a vectogram ("front butterfly") such as the one 160 (FIG. 11) obtained for the regular walking of the example (FIGS. 6 to 8) giving the vertical acceleration (axis 32, g) as a function of the lateral acceleration (axis 33, g). On the front butterfly 160 cyclic paths 161–163 are observed that have a tendency to be all the more superimposed in each other since the walking is regular. In pathological cases, such cyclic paths deviate from each other in an identifiable and analysable manner.

Figure 12:
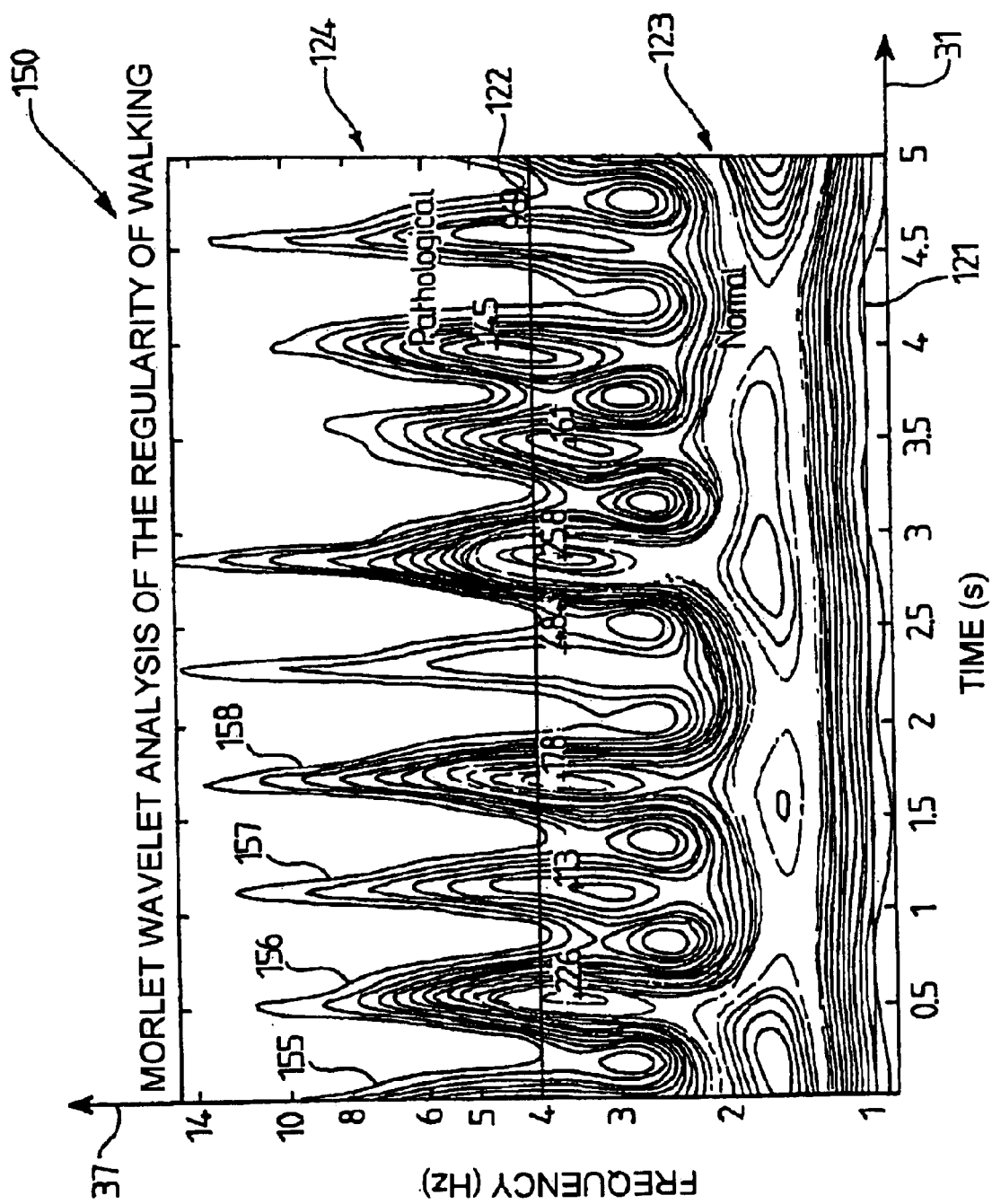
FIG. 12 shows a three dimension spectral image of a Morlet wavelet transform obtained from the vertical acceleration of FIG. 11 according to the analysis method of the invention.
Figure 13:
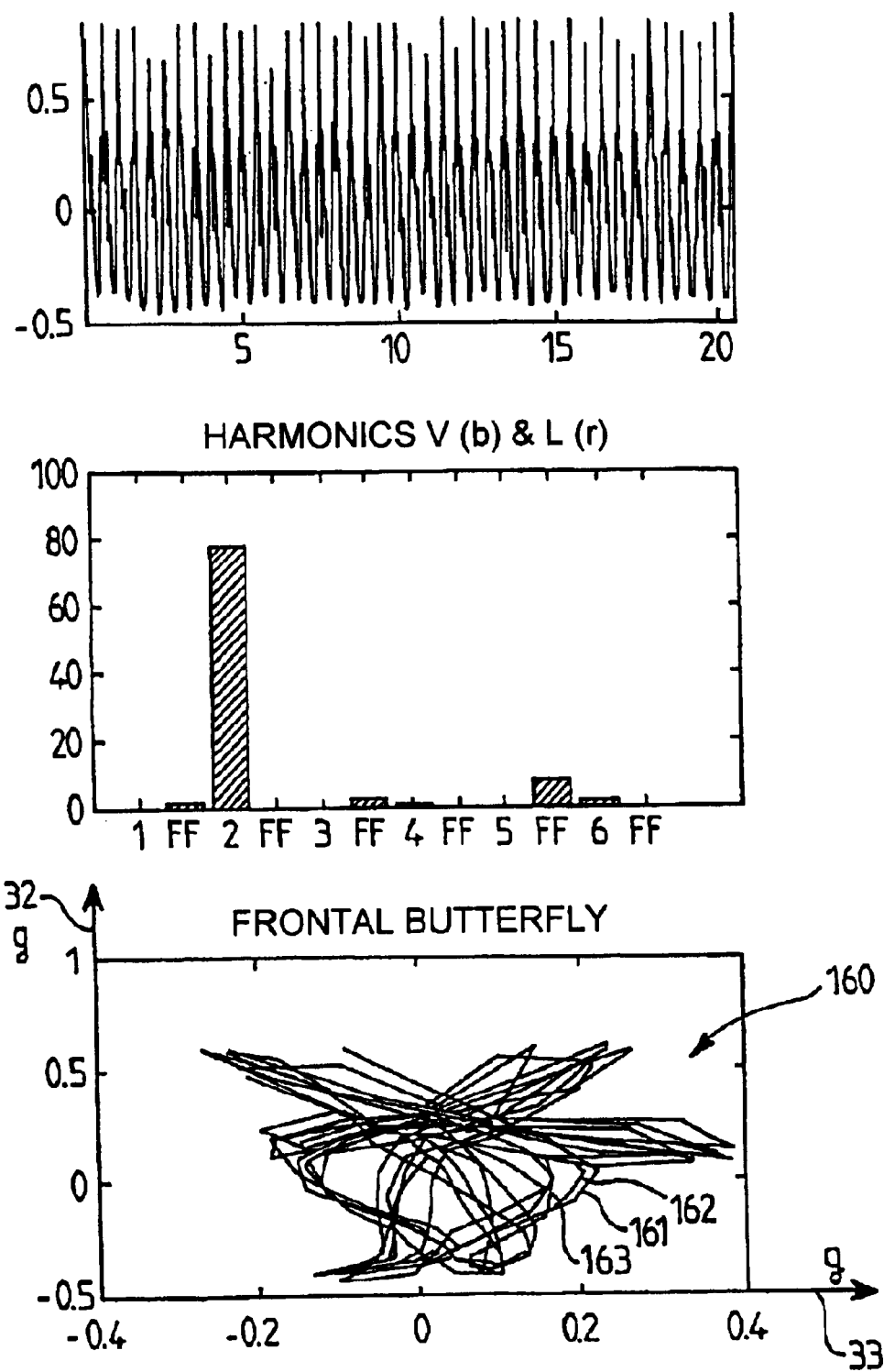
FIG. 13 is a vectogram so-called "front butterfly" giving the vertical acceleration as a function of the lateral acceleration corresponding to the regular walking associated with FIGS. 8 to 10.
Figure 14:
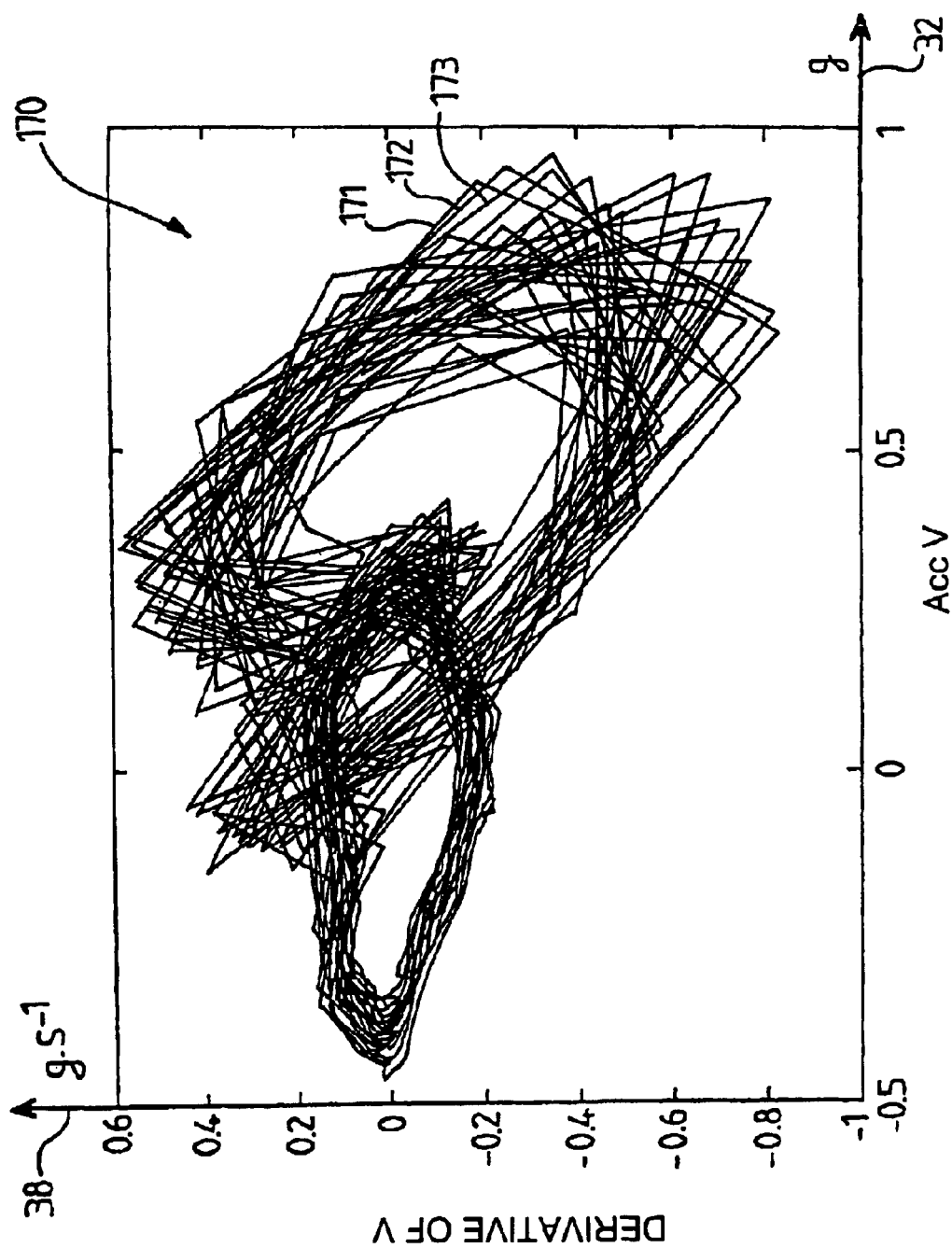
FIG. 14 represents a diagram of the vertical acceleration phases giving the acceleration first derivative in the time as a function of the temporal series of such acceleration for a regular walking corresponding to FIGS. 8 to 10.
Figure 15:
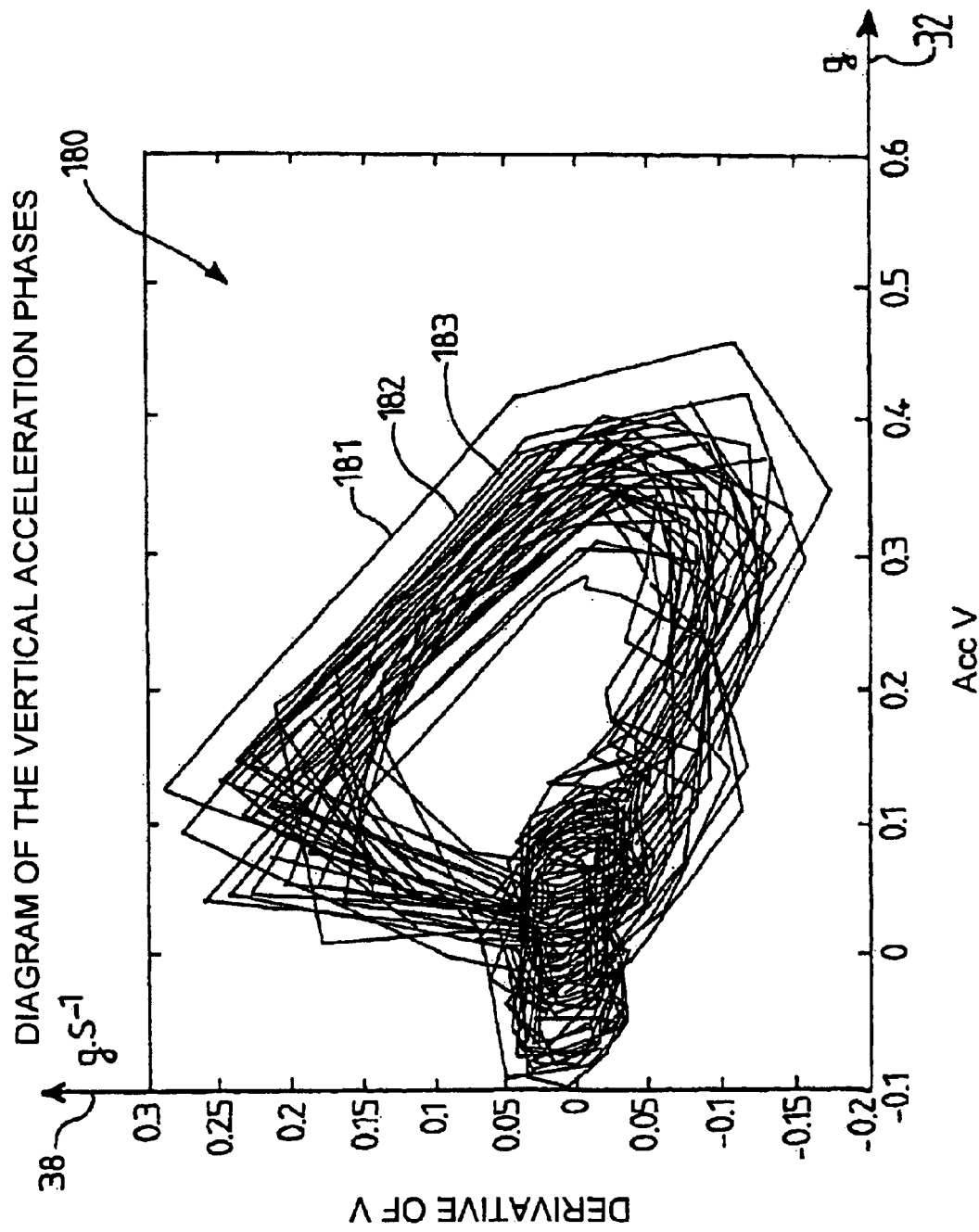
FIG. 15 represents a diagram of the vertical acceleration phases giving the acceleration first derivative in the time as a function of the temporal series of such acceleration for a pathological walking corresponding to FIGS. 11 and 12.

The analysis is also completed by a phase diagram giving for example for the vertical acceleration for regular walking (FIG. 12) and the pathological walking (FIG. 13) given as an example supra, the acceleration derivative (g.s$^{-1}$, axis 38) as a function of the acceleration (g, axis 32). Thus, diagrams 170 and 180 corresponding respectively to regular and pathological walking and having respectively cyclic paths 171–173 and 181–183 are obtained.

The irregular walking of a falling object for example is reflected by a chaotic rate revealed qualitatively by a more pronounced divergence of the cyclic paths 181–183.

The divergence rate of the cyclic paths (or orbits) of the signal is quantified through at least one Lyapunov coefficient. Such a coefficient assesses the sensitivity of a system to deviate from a stationary and periodical regimen from a particular point at a time to where the system characteristics (starting conditions) are known.

The mean Lyapunov coefficient $\lambda_m$ of N−1 Lyapunov coefficients obtained with a sampling interval equal to 1 is conventionally given by a formula as follows:

$$\lambda_m = \frac{\log 2}{N-1} \sum_{n=1}^{N-1} \left( \frac{l_{n+1}}{l_n} \right)$$

wherein:

N is the number of points considered, n is the current point number, and $l_n$ represents the distance between the indexed point n belonging to an orbit and a neighbour closest point belonging to a neighbour orbit in the phase space A practical method for an algorithmic calculation of such a coefficient is for example found in the article from WOLF et al. "Determining Lyapunov exponents from a time series", in review Physica, 16D, 1985, pp. 285–317.

As an example, for a phase space dimension equal to 3 and a sampling interval equal to 3 points, the maximum Lyapunov coefficient calculated on the vertical accelerometric signal is comprised between 0 and 1, such coefficient being all the higher since the pathology increases. Thus, for a value higher than 0.4, walking is quite irregular. This coefficient quantifies the lack of dynamical regularity of the walking cycles and detects the temporal and dynamical fluctuations of co-ordination, in relation with a fall risk.

The whole results obtained from such different methods focussed onto the wavelet analysis are combined to identify the locomotion irregularities and quantify them.

The above-mentioned examples based on the vertical and lateral accelerations for walking are particularly adapted for identifying claudication or degradation of the capacities of elderly people so as to screen early fall risks and to take prevention measures.

In other embodiments, other gaits are taken into consideration and/or other accelerations are used. Thus, for example, a sport walking is analysed by using advantageously the vertical and antero-posterior accelerations of the rachis (sagittal plane of the subject, directions 21 and 23). Preferably, technical defects of a sport walking athlete are thus detected, including a knee flexion at the time of the application and/or a simultaneous broken contact with the ground of both athlete's feet.

In another embodiment, a sport race is analysed. FIGS. 16 and 17 illustrate the three dimensional spectral image of a wavelet transform obtained respectively with a sportsman having a fluidic stride (FIG. 16) and a sportsman having an irregular stride (FIG. 17). FIG. 17 shows on the longitudinal acceleration trace (upper curve <fre pro>) and the corresponding wavelet spectrum (below), a high frequency peak at 0.2–0.4 sec corresponding to an abrupt braking deceleration at the time of the application of the left foot. At the time 0.6–0.8, the application of the right foot does not show any abrupt braking, but a more pronounced propulsion that on the left. Such analyses of the stride allow to visualize and characterize the stride asymmetries and to determine consequently the biomechanical characteristics of an athlete's stride. A comparison of the stride characteristics with the same athlete analysed at two given moments being distant in the time allow to identify the presence of stride abnormalities characterized by changes in his or her biomechanical characteristics. The stride analyses with said athlete according to the method of the invention also allow to quantify and thus to check the functional tolerance of a disease in the locomotive apparatus of the sportsman.

In such embodiment of the method of the invention for the analysis of a sport race, FIG. 18 shows the vertical, antero-posterior and lateral acceleration curves in the time synchronized with the images of the subject.

On those curves the bearing moment (300) of the left leg (G), the mid-bearing moment (301) of the left leg (G), the push moment (302) of the left leg (G), and the end-bearing moment (303) of the left leg (G)

may be identified.

What is claimed is:

1. Method of analysis for human locomotion irregularities, wherein acceleration measurements obtained during at least one motion controlled at a stabilised gait of a human being are used, through at least one accelerometer measuring on a time base at least one acceleration according to at least one direction, by detecting and analysing any locomotion irregularities from reference measurements, characterized in that said measured accelerations are submitted to at least one continuous wavelet transformation and the resulting continuous wavelet transform is used to detect and/or analyse said irregularities, and the spectrum of said continuous wavelet transform is visualised in three dimensions, respectively, of time, frequency and spectral energy module of the continuous wavelet transform to detect and analyse said irregularities.

2. Method of analysis according to claim 1, characterized in that the spectral energy module of the wavelet transform is represented by coloured contours or a colour gradient.

3. Method of analysis according to claim 2, characterized in that a linear scale for time and a logarithmic scale for frequency are used.

4. Method of analysis according to claim 1, characterized in that said transform is a Morlet wavelet transform.

5. Method of analysis according to claim 1, characterized in that the wavelet transform having a time-dependent spectral energy, a low frequency band is defined in which the spectral energy for a regular locomotion is mainly concentrated and said irregularities are detected and/or analysed by using the spectral energy outside such band.

6. Method of analysis according to claim 5, characterized in that the band is comprised between 1 Hz and 4 Hz.

7. Method of analysis according to claim 5, characterized in that irregularities are identified and/or analysed by locating and/or studying the spectral energy peaks (124–128, 155–158) exceeding said band.

8. Method of analysis according to claim 5, characterized in that a locomotion irregularity degree is calculated by reporting the margin spectral energy outside said band to the total spectral energy.

9. Method of analysis according to claim 1, characterized in that said accelerations are at least in a number of two and in that, to detect and/or analyse the irregularities, at least one front butterfly (160) is also used representing the intensity of one of the measured accelerations depending on the intensity of another of the measured accelerations.

10. Method of analysis according to claim 1, characterized in that, to detect and/or analyse the irregularities, at least one representation (170, 180) in a phase space is also used, giving the intensity of at least one of said accelerations depending on the intensity of the time derivative of said acceleration or depending on said acceleration time shifted with a predetermined time (d).

11. Method of analysis according to claim 10, characterized in that at least one Lyapunov coefficient of said representation in the phase space, preferably the maximum Lyapunov coefficient, is calculated.

12. Method of analysis according to claim 11, characterized in that it is considered that a co-ordination disorder occurs if the maximum Lyapunov coefficient is higher than 0.4.

13. Application of the method of analysis according to claim 1 for the medical field, in particular for the early detection of neuro-motor disorders of elderly people.

14. Application of the method of analysis according to claim 1 for the sport field, in particular for detecting technical defects with sport walkers or runners.

15. Application of the method of analysis according to claim 1 for detecting athlete's stride particularities during a race period.

16. Application of the method of analysis according to claim 1 for measuring and quantifying the biomechanical constraints associated to a disease of the locomotive apparatus.

17. Method of analysis for human locomotion irregularities, wherein acceleration measurements obtained during at least one motion controlled at a stabilised gait of a human being are used, through at least one accelerometer measuring on a time base at least one acceleration according to at least one direction, by detecting and analysing any locomotion irregularities from reference measurements, wherein said measured accelerations are submitted to at least one wavelet transformation and the resulting wavelet transform is used to detect and/or analyse said irregularities, and the spectrum of said wavelet transform is visualised in three dimensions, respectively, of time, frequency and spectral energy module of the wavelet transform to detect and analyse said irregularities, characterized in that the wavelet transform having a time-dependent spectral energy, a low frequency band is defined in which the spectral energy for a regular locomotion is mainly concentrated and said irregularities are detected and/or analysed by using the spectral energy outside such band.

18. Method of analysis for human locomotion irregularities, wherein acceleration measurements obtained during at least one motion controlled at a stabilised gait of a human being are used, through at least one accelerometer measuring on a time base at least one acceleration according to at least one direction, by detecting and analysing any locomotion irregularities from reference measurements, wherein said measured accelerations are submitted to at least one wavelet transformation and the resulting wavelet transform is used to detect and/or analyse said irregularities, and the spectrum of said wavelet transform is visualised in three dimensions, respectively, of time, frequency and spectral energy module of the wavelet transform to detect and analyse said irregularities, characterized in that, to detect and/or analyse the irregularities, at least one representation (170, 180) in a phase space is also used, giving the intensity of at least one of said accelerations depending on the intensity of the time derivative of said acceleration or depending on said acceleration time shifted with a predetermined time (d).

\* \* \* \* \*